United States Patent [19]

De Ruiter

[11] Patent Number: Plant 6,243

[45] Date of Patent: Aug. 9, 1988

[54] MINIATURE ROSE PLANT NAMED 'RUIMARSO'

[75] Inventor: Gijsbert De Ruiter, Hazerswoude, Netherlands

[73] Assignee: De Ruiter's Nieuwe Rozen B.V., Hazerswoude, Netherlands

[21] Appl. No.: 887,706

[22] Filed: Jul. 21, 1986

[51] Int. Cl.[4] ..... A01H 5/00

[52] U.S. Cl. ..... Plt./9

[58] Field of Search ..... Plt. 9

*Primary Examiner*—Robert E. Bagwill

*Attorney, Agent, or Firm*—Charles W. Rummler

[57] ABSTRACT

A new variety of miniature rose having a dwarf, compact, free blooming growth habit producing blooms of delicate pink color, approximately 1¾ inches in diameter, with petals of heavy substance, suitable for use as a pot plant.

1 Drawing Sheet

BACKGROUND OF THE NEW PLANT

My new variety of rose plant is a result of breeding efforts carried on by me at Hazerswoude, Holland, with the object of producing a delicate pink rose having an upright growth habit. This plant originated as a seedling derived by my crossing of the variety 'Ruipiko', with an unnamed and unpatented seedling in my greenhouse breeding facilities at Hazerswoude, in Holland. The form and beauty of the flowers of this new plant and its very fine growth habit led me to propagate this plant through several generations, by budding, which shows that the novel characteristics of this plant would hold true from generation to generation and as a result, commercial propagation of this plant, by budding, in now being carried on under my direction in Holland.

DESCRIPTION OF THE DRAWINGS

My new variety of rose plant is illustrated by the accompanying photographic drawings, which show vegetative growth and flowers of this variety during July 1985 as true in color as is reasonably possible to make in a color illustration of this character. The specimens illustrated were grown with three plants in one pot in a greenhouse at Hazerswoude, Holland.

DESCRIPTION OF THE NEW PLANT

The following combination of characteristics is observed in the new variety:

(a) Readily propagated and grown on its own roots by cuttings;

(b) Exhibits a well balanced, compact, vigorous growth habit which is extremely floriferous;

(c) Blooms carried one per stem, sometimes also in small cluster;

(d) Exhibits an excellent aptitude for greenhouse forcing as a flowering pot plant;

(e) Bloom color in general delicate pink fading to a lighter shade.

The following is a detailed description of my new rose plant and throughout this specification, color designations are according to The R.H.S. Colour Chart published by The Royal Horticultural Society of London, England.

THE PLANT

Origin: Seedling.

Parentage:
- *Seed parent.*—'Ruipiko'.
- *Pollen parent.*—Unnamed variety.

Classification:
- *Botanic.*—Hybrid rose.
- *Commercial.*—Miniature rose.

Form: Bush.

Habit: Upright and much branched.

Growth: Vigorous, dwarf.

Height: 20 to 25 cm.

Foliage:
- *Quantity.*—Abundant.
- *Number of leaves.*—Usually 5, occasionally 7.
- *Size.*—Small. Length — About 45 to 65 mm. Width — About 35 to 40 mm.
- *Quantity.*—Normal.
- *Color.*—New foliage — Yellow-Green, 146A. Reverse side — Reddish. Old foliage — Yellow-Green, 147A.

Leaflets:
- *Shape.*—Ovate.
- *Texture.*—Firm.
- *Margin.*—Serrated.
- *Serration.*—Double, medium.
- *Shape of base of terminal leaflet.*—Rounded.
- *Petiole.*—Color: Green with very few prickles on under side.
- *Stipules.*—Small, slightly bearded.

Thorns:
- *Quantity.*—On main canes from base — Very few. On laterals from main canes — Very few.
- *Form.*—Concave, Thin.
- *Color when young.*—Light green.

Small thorns:
- *Quantity.*—On main stalks — None. On laterals — None.

New wood:
- *Color.*—Green.
- *Texture.*—Bark, smooth.

Old wood:
- *Color.*—Greyish-green.
- *Texture.*—Bark, smooth.

THE BUD

Form: Ovate.

Size:
- *Diameter.*—About 10 mm. and about 12 mm. when the petals start to unfurl.

*Length.*—About 13 to 15 mm.

Color:

*When sepals first divide.*—Orange, 29C.

*When half blown.*—Upper side, Red, 37D; under side, Red, 38B.

Sepals: Extensions absent in three, medium in two.

*Margins.*—Hairy.

Receptacle:

*Shape.*—Pitcher shaped.

*Size.*—Small. Length — About 3 mm. Width — About 3 mm.

*Surface.*—Smooth.

*Aspect.*—Dull.

*Color.*—Yellow-Green, 144B.

*Peduncle.*—Length: About 38 mm.

THE FLOWER

Blooming habit: Continuous and abundant.

Borne: Singly and a few small clusters.

Size:

*Diameter.*—About 4.5 cm.

Form:

*Upper part.*—Convex.

*Lower part.*—Flat.

Petalage:

*Number of petals.*—40 to 60.

*Shape.*—Broad.

*Texture.*—Medium thick and firm.

*Arrangement.*—Imbricated.

*Color.*—Upper side of petals: Marginal zone, Red, 55D-56B. Middle zone, Red, 56B-55D. Basal zone, Red, 56B. Basal spot, Yellow, 10D. Reverse side of petals: Marginal zone, Red, 39D-49D. Middle zone, Red, 49D-39D. Basal zone, Orange, 27C. Basal spot, Yellow, 10D.

Discoloration after full bloom: The flower becomes Red, 49B, after 10 to 14 days.

Fragrance: None

Persistence: Dries when overblown.

Lasting quality: Long lasting on the plant.

REPRODUCTIVE ORGANS

Stamens:

*Anthers.*—Number: 45 to 50. Arrangement: Regular around the styles. Length: Short Color: Yellow-Orange, 16D.

*Filaments.*—Length: About 2 to 3 mm. Color: Yellow-Green, 145C.

*Pollen.*—Color: Yellow-Orange, 15B.

Pistils:

*Styles.*—Number: About 30 to 40. Length: About 5 to 6 mm. Color: Yellow-Green, 145C.

Character of ovaries: Normal.

I claim:

1. A new and distinct variety of rose plant of the miniature class, substantially as herein shown and described, characterized by its dwarf, compact, free blooming growth habit, producing blooms of delicate pink color of about 4.5 centimeters in diameter, the blooms having petals of heavy substance and the plant being suitable for use as a pot plant.

* * * * *

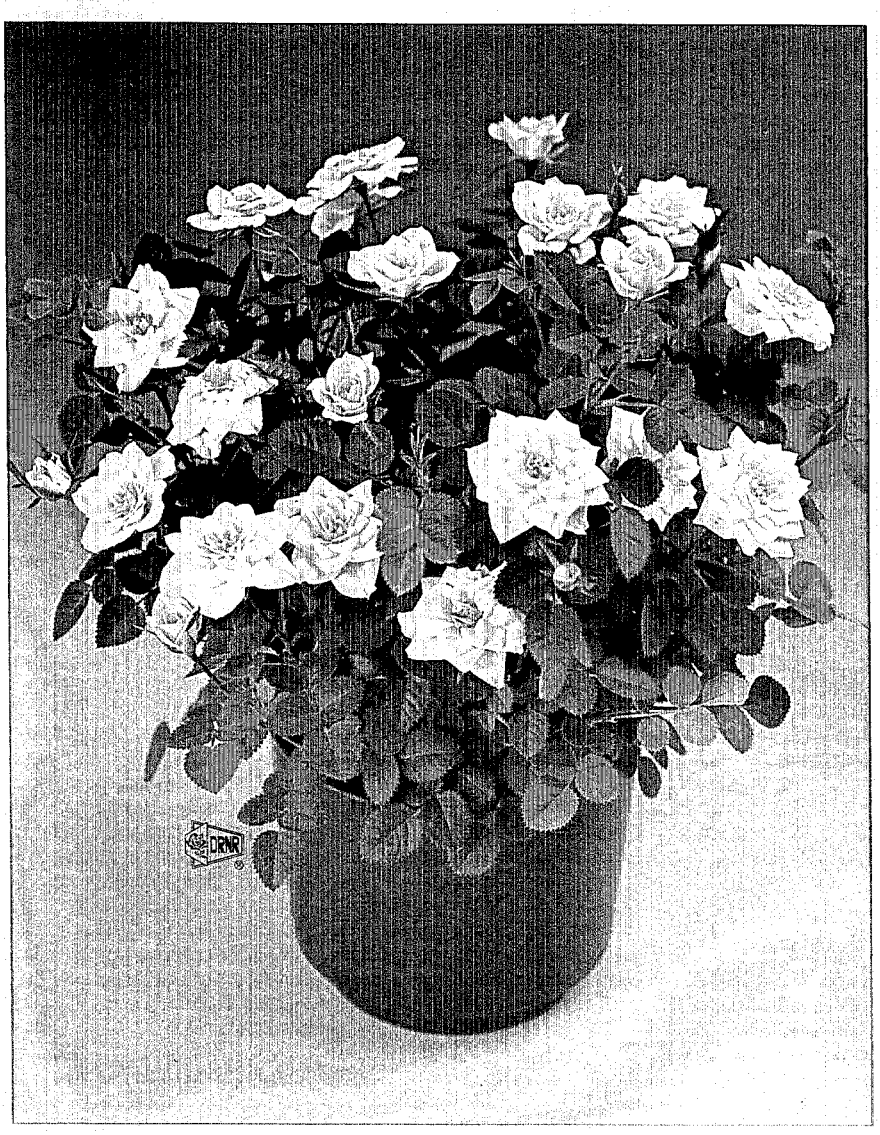
DRNR